(12) United States Patent
Nixon et al.

(10) Patent No.: US 11,499,973 B2
(45) Date of Patent: Nov. 15, 2022

(54) METHODS OF PREDICTING RESPONSIVENESS OF A CANCER TO A VEGF TARGETING AGENT AND METHODS OF PROGNOSING AND TREATING CANCER

(71) Applicant: Duke University, Durham, NC (US)

(72) Inventors: Andrew Nixon, Durham, NC (US); Chris Brady, Durham, NC (US); Yingmiao Liu, Durham, NC (US); Herbert Hurwitz, Durham, NC (US); Kouros Owzar, Durham, NC (US); Alexander Sibley, Durham, NC (US); Chen Jiang, Durham, NC (US); Ace Hatch, Durham, NC (US); Mark Starr, Durham, NC (US)

(73) Assignee: Duke University, Durham, NC (US)

( * ) Notice: Subject to any disclaimer, the term of this patent is extended or adjusted under 35 U.S.C. 154(b) by 389 days.

(21) Appl. No.: 16/302,343

(22) PCT Filed: May 17, 2017

(86) PCT No.: PCT/US2017/033112
§ 371 (c)(1),
(2) Date: Nov. 16, 2018

(87) PCT Pub. No.: WO2017/201166
PCT Pub. Date: Nov. 23, 2017

(65) Prior Publication Data
US 2019/0204320 A1    Jul. 4, 2019

Related U.S. Application Data

(60) Provisional application No. 62/337,633, filed on May 17, 2016, provisional application No. 62/337,542, filed on May 17, 2016.

(51) Int. Cl.
| | |
|---|---|
| *A61K 39/00* | (2006.01) |
| *G01N 33/574* | (2006.01) |
| *C07K 16/22* | (2006.01) |
| *A61K 31/513* | (2006.01) |
| *A61K 31/519* | (2006.01) |
| *A61K 31/555* | (2006.01) |
| *C12Q 1/6886* | (2018.01) |
| *A61P 35/00* | (2006.01) |
| *C07K 16/28* | (2006.01) |
| *A61K 45/06* | (2006.01) |

(52) U.S. Cl.
CPC ..... *G01N 33/57419* (2013.01); *A61K 31/513* (2013.01); *A61K 31/519* (2013.01); *A61K 31/555* (2013.01); *A61P 35/00* (2018.01); *C07K 16/22* (2013.01); *C07K 16/2863* (2013.01); *C12Q 1/6886* (2013.01); *G01N 33/574* (2013.01); *A61K 45/06* (2013.01); *A61K 2039/505* (2013.01); *A61K 2039/55* (2013.01); *C07K 2317/24* (2013.01); *C07K 2317/76* (2013.01); *C12Q 2600/106* (2013.01); *C12Q 2600/158* (2013.01); *G01N 2800/52* (2013.01)

(58) Field of Classification Search
CPC ... G01N 33/574; A61P 35/00; C07K 16/2863; C07K 16/22; C12Q 2600/158
See application file for complete search history.

(56) References Cited

U.S. PATENT DOCUMENTS

| | | | |
|---|---|---|---|
| 9,255,927 B2 | 2/2016 | Nixon | |
| 9,869,677 B2 | 1/2018 | Nixon | |
| 2006/0223770 A1 | 10/2006 | Fougerolles et al. | |
| 2010/0055099 A1 | 3/2010 | Filvaroff | |
| 2011/0076271 A1 | 3/2011 | Schmidt | |
| 2011/0257035 A1 | 10/2011 | Pena | |
| 2012/0142012 A1 | 6/2012 | Hacker | |
| 2013/0177564 A1 | 7/2013 | Carmeliet | |
| 2014/0127193 A1* | 5/2014 | Nixon | A61K 31/7068 424/133.1 |
| 2014/0178363 A1 | 6/2014 | Ferrara | |
| 2016/0024585 A1 | 1/2016 | Nixon | |

FOREIGN PATENT DOCUMENTS

| | | |
|---|---|---|
| EP | 2293071 | 3/2011 |
| WO | 2009155504 | 12/2009 |
| WO | 2010048304 | 4/2010 |
| WO | 2012151574 | 11/2012 |
| WO | WO2012151574 | * 11/2012 |

OTHER PUBLICATIONS

Weickhartt et al., BJC 113:37-45, published online Jun. 30, 2015 (Year: 2015).*
Lieu et al. (PLOS One, 8: (10) e77117 (Year: 2013).*
Fisher et al, Cell 131: 463-475, 2007). (Year: 2007).*
Emmanouilides et al, BMC Cancer, 7:91, 2007) (Year: 2007).*
Huynh H, et al.: Estradiol and antiestrogens regulate a growth inhibitory insulin-like growth factor binding protein 3 autocrine loop in human breast cancer cells. J Biol Chem 271:1016-21, 1996.
International Searching Authority. International Search Report and Written Opinion for application PCT/US2017/033112. dated Aug. 17, 2017. 11 pages.

(Continued)

*Primary Examiner* — Lei Yao
(74) *Attorney, Agent, or Firm* — Quarles & Brady LLP (57) ABSTRACT

Methods of predicting responsiveness of a cancer in a subject to a cancer therapy including a VEGF targeting agent are provided. The methods may include obtaining a sample from the subject, determining an expression level of at least one biomarker selected from the group consisting of VEGF-D and PlGF in a sample from the subject, comparing the expression level of the biomarker in the sample to a reference level of the biomarker, and predicting the responsiveness of the cancer to treatment with the cancer therapy including a VEGF targeting agent. Optionally, the methods may further include administering a VEGF target agent and/or an anticancer or chemotherapy agent to the subject. Additional methods of prognosing and treating a cancer in a subject are also provided.

7 Claims, 5 Drawing Sheets

(56) References Cited

OTHER PUBLICATIONS

Kaaks R, et al.: Serum C-peptide, insulin-like growth factor (IGF)-I, IGF-binding proteins, and colorectal cancer risk in women. J Natl Cancer Inst 92:1592-600., 2000.
Kang, M.J., et al. Biweekly cetuximab plus irinotecan as second-line chemotherapy for patients with irinotecan-refractory and KRAS wild-type metastatis colorectal cancer according to epidermal growth factor receptor expression status. Invest New Drugs (2012) 30:1607-1613.
Kapitanovic S, et al. The expression of p185(HER- 2/neu) correlates with the stage of disease and survival in colorectal cancer. Gastroenterology 1997; 112:1103-1113.
Kay EW, et al. Cytoplasmic c-erb-B-2 protein expression correlates with survival in Dukes' B colorectal carcinoma. Histopathology 1994; 25:455-461.
Kluftinger AM, et al. Correlation of epidermal growth factor receptor and c-erb-B2 oncogene product to known prognostic indicators of colorectal cancer. Surg Oncol 1992; 1:97-105.
Koenuma M, et al.: Insulin and insulin-like growth factor 1 stimulate proliferation of metastatic variants of colon carcinoma 26. Jpn J Cancer Res 80:51-8, 1989.
Kopetz, S. et al., "Phase II trial of infusional fluorouracil, irinotecan, and bevacizumab for metastatic colorectal cancer: efficacy and circulating angiogenic biomarkers associated with therapeutic resistance," J Clin Oncol (2010) 28:453-9.
Liang JT, et al. High-frequency microsatellite instability predicts better chemosensitivity to high-dose 5-fluorouracil plus leucovorin chemotherapy for stage IV sporadic colorectal cancer after palliative bowel resection. Int J Cancer. 2002;101:519-25.
Lieu, C.H., et al., "Relative impact of chemotherapy with or without bevacizumab on cytokines and angiogenic factors (CAFs) in metastatic colorectal cancer," J Clin Oncol (2011) 29:(suppl 4; Abstract 401) (Abstract).
Lieu, C.H., et al., "The association of alternate VEGF ligands with resistance to anti-VEGF therapy in metastatic colorectal cancer," PLoS One (2013) 8(10): p. e77117.
Liu, Y., et al., "Correlation of angiogenic biomarker signatures with clinical outcomes in metastatic colorectal cancer patients receiving capecitabine, oxaliplatin, and bevacizumab," Cancer Med. (2013) 2(2):234-42.
Ma J, et al: Prospective study of colorectal cancer risk in men and plasma levels of insulin-like growth factor (IGF)-I and IGF-binding protein-3. J Natl Cancer Inst 91:620-5, 1999.
Mayer A, et al. The prognostic significance of proliferating cell nuclear antigen, epidermal growth factor receptor, and mdr gene expression in colorectal cancer. Cancer 1993; 71:2454- 2460.
Mckay JA, et al. Evaluation of the epidermal growth factor receptor (EGFR) in colorectal tumours and lymph node metastases. Eur J Cancer. 2002;38:2258-64.
Mcleod HL, et al. Tumour markers of prognosis in colorectal cancer. Br J Cancer. 1999;79:191-203.
Metzger R, et al. ERCC1 mRNA levels complement thymidylate synthase mRNA levels in predicting response and survival for gastric cancer patients receiving combination cisplatin and fluorouracil chemotherapy. J Clin Oncol. 1998;16:309-16.
Nixon, A.B., et al., "Prognostic and predictive blood-based biomarkers in patients with advanced pancreatic cancer: Results from CALGB80303 (Alliance)," Clin Cancer Res. (2013) 19(24):6957-66.
Nixon, A.B. et al. "Blood-based biomarkers in patients (pts) with metastatic colorectal cancer (mCRC) treated with FOLFOX or FOLFIRI plus bevacizumab (Bev), cetuximab (Cetux), or bev plus Cetux: Results from CALGB 80405 (Alliance)," J Clin Oncol 34, 2016 (suppl; abstr 3597).
Pollak M, et al.: Effect of tamoxifen on serum insulinlike growth factor I levels in stage I breast cancer patients. J Natl Cancer Inst 82:1693-7, 1990.
Poon, M. A., et al. (1991). "Biochemical modulation of fluorouracil with leucovorin: confirmatory evidence of improved therapeutic efficacy in advanced colorectal cancer." J Clin Oncol 9:1967-1972.
Remacle-Bonnet MM, et al: Insulin-like growth factor-1 protects colon cancer cells from death factor-induced apoptosis by potentiating tumor necrosis factor alpha-induced mitogen-activated protein kinase and nuclear factor kappaB signaling pathways. Cancer Res 60:2007-17, 2000.
Rosenberg, A. H., et al. (2002). "Erbitux (IMC-C225) plus weekly irinotecan (CPT-11), fluorouracil (5FU) and leucovorin (LV) in colorectal cancer that expresses the epidermal growth factor receptor (EGFr)." Proc ASCO 21: 135a.
Rothenberg, M, et al. Superiority of oxaliplatin and fluorouracil-leucovorin compared with either therapy alone in patients with progressive colorectal cancer after irinotecan and fluorouracil-leucovorin: Interim results of a phase III trial. J Clin Oncol 2003: 21:2059-2069.
Saltz L, et al. Cetuximab (IMC-225) plus irinotecan (IRINOTECAN) is active in IRINOTECAN refractory colorectal cancer (CRC) that expresses epidermal growth factor receptor (EGFR). Proc Am Soc Clin Oncol 2001; 20:3a, abstract 7.
Saltz, L., et al. (2002). "Single agent IMC225 (Erbitux) has activity in CPT-11 refractory colorectal cancer that expresses epidemral growth factor receptor (EGFR)." Proc ASCO 21:127a.
Schoffski, P., et al. (2002). "Cetuximab (C225) plus irnotecan (CPT-11) plus infusional 5FU-folinic acid is safe and active in metastatic colorectal cancerthat expresses epdiermal growth factor receptor (EGFR)." Proc ASCO 21: 159a.
Shitara, K., et al. Phase II study of combination chemotherapy with biweekly cetuximab and irinotecan for wild-type KRAS metastatic colorectal cancer refractory to irinotecan, oxaliplatin, and fluoropyrimidines. Invest. New Drugs (2012) 30:787-793.
Tol, J., et al. "A randomised phase III study on capecitabine, oxaliplatin and bevacizumab with or without cetuximab infirst-line advanced colorectal cancer, the CAIRO2 study of the Dutch Colorectal Cancer Group (DCCG). An interim analysis of toxicity." Annals of Oncology 19.4 (2008): 734-738.
Tournigand, C., et al. (2001). "FOLFIRI followed by FOLFOX versus FOLFOX followed by FOLFIRI in metastatic colorectal cancer: final results of a phase III study." Proc ASCO 20: 124a.
Venook, A.P., et al., CALGB/SWOG 80405: Phase III trial of irinotecan/5-FU/leucovorin (FOLFIRI) or oxaliplatin/5-FU/leucovorin (mFOLFOX6) with bevacizumab (BV) or cetuximab (GET) for patients (pts) with KRAS wild-type (wt) untreated metastatic adenocarcinoma of the colon or rectum (MCRC). J Clin Oncol, 2014. 32: p. suppl; abstr LBA3.
Watanabe T, et al. Molecular predictors of survival after adjuvant chemotherapy for colon cancer. N Engl J Med. 2001;344:1196-206.
Weickhardt A.J. et al., "Vascular endothelial growth factors (VEGF) and VEGF receptor expression as predictive biomarkers for benefit with bevacizumab in metastatic colorectal cancer (mCRC): Analysis of the phase III Max study," J Clin Oncol. (2011) 29:3531 (suppl; Abstract).
Wu Y, et al: Circulating insulin-like growth factor-I levels regulate colon cancer growth and metastasis. Cancer Res 62:1030-5., 2002.
Aaronson SA: Growth factors and cancer. Science 254:1146-53, 1991.
Abbasi AA, et al: Low circulating levels of insulin-like growth factors and testosterone in chronically institutionalized elderly men. J Am Geriatr Soc 41:975-82, 1993.
Achille E, et al.: FOLFIRI Followed by FOLFOX or FOLFOX Followed by FOLFIRI in Metastatic Colorectal Cancer: Which Is the Best Sequence? Safety and Preliminary Efficacy Results of a Randomized Phase IIIStudy., Proc Am Soc Clin Oncol, 2000.
Adlard JW, et al. Prediction of the response of colorectal cancer to systemic therapy Lancet Oncol. 2002;3:75-82.
Allegra C. Thymidylate synthase levels: prognostic, predictive, or both? J Clin Oncol. 2002;20:1711-3.
Allegra CJ, et al. Prognostic Value of Thymidylate Synthase, Ki-67, and p53 in Patients With Dukes' B & C Colon Cancer: A National Cancer Institute- National Surgical Adjuvant Breast and Bowel Project Collaborative Study. J Clin Oncol. 2003;21:241-50.

(56) References Cited

OTHER PUBLICATIONS

Arber N, et al.: Nonsteroidal anti-inflammatory drugs and prevention of colorectal cancer. Curr Gastroenterol Rep 1:441-8., 1999.
Baron JA, et al.: Calcium supplements for the prevention of colorectal adenomas. Calcium Polyp Prevention Study Group. N Engl J Med 340:101-7., 1999.
Baselga J, et al. Activated epidermal growth factor receptor: studies in head and neck tumors and tumor cell lines after exposure to ligand and receptor tyrosine kinase inhibitors. Proc Am Soc Clin Oncol 1999, abstr 2392.
Baselga J. The EGFR as a target for anticancer therapy—focus on cetuximab. Eur J Cancer 2001; 37:S16-S22.
Baserga R: The insulin-like growth factor 1 receptor: a key to tumor growth? Cancer Res 55:249-52, 1995.
Boonsong A, et al. Topoisomerase I protein expression in primary colorectal cancer and lymph node metastases. Hum Pathol. 2002;33:1114-9.
Bras-Goncalves RA, et al. Sensitivity to CPT-11 of xenografted human colorectal cancers as a function of microsatellite instability and p53 status. Br J Cancer. 2000;82:913-23.
Brown J, et al.: Nutrition during and after cancer treatment: a guide for informed choices by cancer survivors. CA Cancer J Clin 51:153-87. 2001.
Buerger H, et al. Length and loss of heterozygosity of an intron 1 polymorphic sequence of egfr is related to cytogenetic alterations and epithelial growth factor receptor expression. Cancer Res. 2000;60:854-7.
Burroughs KD, et al: Insulin-like growth factor-I: a key regulator of human cancer risk? J Natl Cancer Inst 91:579-81, 1999.
Caan BJ, et al: Body size and the risk of colon cancer in a large case-control study. Int J Obes Relat Metab Disord 22:178-84., 1998.
Damoriano JK, et al: Weight change in women treated with adjuvant therapy or observed following mastectomy for node-positive breast cancer. J Clin Oncol 8:1327-34., 1990.
Cascinu S, et al.: Neuroprotective effect of reduced glutathione on oxaliplatin-based chemotherapy in advanced colorectal cancer: a randomized, double-blind, placebo-controlled trial. J Clin Oncol 20:3478-83, 2002.
Chan JM, et al: Plasma insulin-like growth factor-I and prostate cancer risk: a prospective study. Science 279:563-6, 1998.
Chang KM, et al.: Epidermal growth factor in gingival crevicular fluid and its binding capacity in inflamed and non-inflamed human gingiva. Arch Oral Biol 41:719-24, 1996.
Chinery R, et al.: Antioxidants enhance the cytotoxicity of chemotherapeutic agents in colorectal cancer: a p53-independent induction of p21WAF1/CIP1 via C/EBPbeta. Nat Med 3:1233-41, 1997.
Chlebowski RT, et al.: Long-term survival following relapse after 5-FU but not CMF adjuvant breast cancer therapy. Breast Cancer Res Treat 7:23-30, 1986.
Chute CG, et al.: A prospective study of body mass, height, and smoking on the risk of colorectal cancer in women. Cancer Causes Control 2:117-24., 1991.
Chyou PH, et al: A prospective study of colon and rectal cancer among Hawaii Japanese men. Ann Epidemiol 6:276-82., 1996.
Colditz GA, et al: Validation of questionnaire information on risk factors and disease outcomes in a prospective cohort study of women. Am J Epidemiol 123:894-900, 1986.
Collie-Duguid ES, et al. Thymidine phosphorylase and dihydropyrimidine dehydrogenase protein expression in colorectal cancer. Int J Cancer. 2001;94:297-301.
Comba, A. Z., et al. (2001). "A randomised phase II study of oxaliplatin alone versus oxaliplatin combined with 5-fluorouracil and folinic acid (Mayo Clinic regimen) in previously untreated metastatic colorectal cancer patients." Eur J Cancer 37: 1006-1013.
Cui Y, et al: Body mass and stage of breast cancer at diagnosis. Int J Cancer 98:279-83., 2002.
Culouscou JM, et al.: Simultaneous production of IGF-I and EGF competing growth factors by HT-29 human colon cancer line. Int J Cancer 40:646-52, 1987.

Cunningham, D., et al. (1998). "Randomised trial of irinotecan plus supportive care versus supportive care alone after fluorouracil failure for patients with metastatic colorectal cancer." Lancet 352:1413-1418.
Cushman, S.M. et al., "Gene expression markers of efficacy and resistance to cetuximab treatment in metastatic colorectal cancer: Results from CALGB 80203 (Alliance)," Clinical Cancer Research (2014) 21(5):1078-1086.
Cushman, S.M. et al., "Tumor markers of efficacy and resistance to cetuximab treatment in metastatic colorectal cancer: Results from CALGB 80203 (Alliance)," Presented at ASCO Annual 2013 Meeting.
Daling JR, et al: Relation of body mass index to tumor markers and survival among young women with invasive ductal breast carcinoma. Cancer 92:720-9, 2001.
De Gramont A, et al: Leucovorin and fluorouracil with or without oxaliplatin as first-line treatment in advanced colorectal cancer. J Clin Oncol 18:2938-47, 2000.
De Jong JK, et al. Clinical relevance of transforming growth factor alpha, epidermal growth factor receptor, p53, and Ki67 in colorectal liver metastases and corresponding primary tumors. Hepatology 1998; 28:971-979.
Douillard JY, et al: Irinotecan combined with fluorouracil compared with fluorouracil alone as first-line treatment for metastatic colorectal cancer: a multicentre randomised trial. Lancet 355:1041-7, 2000.
Elsaleh H, et al. P53 alteration and microsatellite instability have predictive value for survival benefit from chemotherapy in stage III colorectal carcinoma. Clin Cancer Res. 2001;7:1343-9.
Franceschi S, et al: Dietary glycemic load and colorectal cancer risk. Ann Oncol 12:173-8., 2001.
Geier A, et al: Insulin-like growth factor-1 inhibits cell death induced by anticancer drugs in the MCF-7 cells: involvement of growth factors in drug resistance. Cancer Invest 13:480-6, 1995.
George, et al., "VEGF-A, VEGF-C, VEGF-D in colorectal cancer progression," Neoplasia (2001) 3(5):420-427.
Gill GN, et al. Monoclonal anti-epidermal growth factor receptor antibodies which are inhibitors of epidermal growth factor binding and antagonists of epidermal growth factor-stimulated tyrosine protein kinase activity. J Biol Chem 1984; 259:7755-7760.
Giovannucci E, et al: A prospective study of plasma insulin- like growth factor-1 and binding protein-3 and risk of colorectal neoplasia in women. Cancer Epidemiol Biomarkers Prev 9:345-9, 2000.
Goede, V. et al., "Identification of serum angiopoietin-2 as a biomarker for clinical outcome of colorectal cancer patients treated with bevacizumab-containing therapy," British Journal of Cancer (2010) 103:1407-1414.
Goldberg, R. (2002). N9741: oxaliplatin (oxal) or CPT-11 + 5-fluorouracil (5FU)/leucovorin (LV) or oxal+ CPT-11 in advanced colorectal cancer. Initial toxicity and response data from a GI Intergroup study. In Proc. Am Soc Clin Oncol (vol. 21, pp. 128a-511).
Goldstein NI, et al. Biological efficacy of a chimeric antibody to the epidermal growth factor receptor in a human tumor xenograft model. Clin Cancer Res 1995; 1:1311-1318.
Goldstein NS, et al. Epidermal growth factor receptor immunohistochemical reactivity in patients with American Joint Committee on Cancer stage IV colon adenocarcinoma. Cancer 2001; 92:1331-1346.
Gooch JL, et al: Insulin-like growth factor (IGF)-I rescues breast cancer cells from chemotherapy-induced cell Jeath-proliferative and anti- apoptotic effects. Breast Cancer Res Treat 56:1-10, 1999.
Guo YS, et al: Characterization of insulinlike growth factor I receptors in human colon cancer. Gastroenterology 102:1101-8, 1992.
Hatch, A.J. et al., Blood-based markers of efficacy and resistance to cetuximab treatment in metastatic colorectal cancer: Results from CALGB 80203 (Alliance), Cancer Medicine (Jul. 27, 2016) doi: 10.1002/cam4.806. [Epub ahead of print].

* cited by examiner

METHODS OF PREDICTING RESPONSIVENESS OF A CANCER TO A VEGF TARGETING AGENT AND METHODS OF PROGNOSING AND TREATING CANCER

CROSS-REFERENCE TO RELATED PATENT APPLICATIONS

The present application is a national stage filing under 35 U.S.C. 371 of International Application No. PCT/US2017/033112, filed May 17, 2017, which claims the benefit of priority to U.S. Provisional Patent Application No. 62/337,633, filed on May 17, 2016, and U.S. Provisional Patent Application No. 62/337,542, filed on May 17, 2016, the contents of which are incorporated herein by reference in their entireties.

INTRODUCTION

Agents that inhibit either VEGF signaling pathways or mitogenic signaling through the epidermal growth factor receptor (EGFR) pathway are among the most widely used targeted therapeutics in oncology. Bevacizumab, an antibody against vascular endothelial growth factor A (VEGF-A), and cetuximab, an antibody against the extracellular domain of EGFR, are both approved as treatments for various types of cancer. However, predictive and prognostic biomarkers are still needed to direct selection of the ideal therapeutic regimen for any individual patient. Cancer and Leukemia Group B (CALGB), now part of The Alliance for Clinical Trials in Oncology cooperative group, and SWOG (the Southwest Oncology Group), conducted CALGB/SWOG 80405 in an attempt to provide the key data needed to better guide clinical decision making in this patient population.

SUMMARY

In one aspect of the present invention, methods of predicting responsiveness of a cancer in a subject to a cancer therapy including a VEGF targeting agent are provided. The methods may include obtaining a sample from the subject, determining an expression level of at least one biomarker selected from the group consisting of VEGF-D and PlGF in a sample from the subject, comparing the expression level of the biomarker in the sample to a reference level of the biomarker, and predicting the responsiveness of the cancer to treatment with the cancer therapy including a VEGF targeting agent. Optionally, the methods may further include administering a VEGF targeting agent and/or an anticancer agent to the subject.

In another aspect, the present invention relates to methods of developing a prognosis for a subject diagnosed with a cancer. The methods may include determining an expression level of at least one biomarker selected from the group consisting of Ang-2, CD-73, HGF, ICAM-1, IL-6, OPN, TIMP-1, TSP-2, VCAM-1, and VEGFR-3 in a sample from the subject, comparing the expression levels of the at least one biomarker in the sample to reference levels, and determining an outcome or survival prognosis for the subject. The subject may or may not be treated with a VEGF-targeting agent or an EGFR targeting agent.

In a further aspect, methods are provided. The methods may include obtaining a sample from the subject, and determining an expression level of at least one, two, three, four, five, six, seven, eight, nine, ten, eleven, or twelve biomarker(s) selected from the group consisting of VEGF-D, PlGF, Ang-2, CD-73, HGF, ICAM-1, IL-6, OPN, TIMP-1, TSP-2, VCAM-1, and VEGFR-3 in a sample from the subject.

In a still further aspect, methods of treating cancer in a subject are provided. The methods may include administering to the subject a therapeutically effective amount of a VEGF targeting agent based on an expression level of VEGF-D, PlGF, or both in a sample from the subject. Optionally, the methods may further include administering one or more anticancer agent to the subject.

BRIEF DESCRIPTION OF THE DRAWINGS

FIG. 2 shows the forest plots for the prognostic markers for OS (FIG. 2A) and PFS (FIG. 2B).

FIG. 5 shows the VEGF-D forest plots for OS (FIG. 5A) and PFS (FIG. 5B) evaluated by quartile.

DETAILED DESCRIPTION

Cancer and Leukemia Group B (CALGB), now part of The Alliance for Clinical Trials in Oncology cooperative group, and SWOG (the Southwest Oncology Group), conducted CALGB/SWOG 80405 ("CALGB 80405") to compare bevacizumab, cetuximab, and the combination of both agents. The clinical results of CALGB 80405 were recently published (Venook, A. P., et al., *CALGB/SWOG 80405: Phase III trial of irinotecan/5-FU/leucovorin (FOLFIRI) or oxaliplatin/5-FU/leucovorin (mFOLFOX6) with bevacizumab (B V) or cetuximab (CET) for patients (pts) with KRAS wild-type (wt) untreated metastatic adenocarcinoma of the colon or rectum (MCRC).* J Clin Oncol, 2014. 32: p. suppl; abstr LBA3) showing similar progression-free survival (PFS) and overall survival (OS) benefits from either bevacizumab or cetuximab therapy. The combination regimen was discontinued due to increased toxicity and the release of results from CAIRO2 showing lack of increased survival benefit from the combination of these two agents. See N Engl J Med 2009; 360:563-572; Ann Oncol. 2008 April; 19(4):734-8. Other than KRAS status, no other molecular biomarkers exist to select the most appropriate therapeutic agent for treating colorectal cancer.

Blood-based biomarkers are appealing as sources of clinically-relevant information because blood samples can be obtained at low cost, are of minimal risk to patients, and samples can be collected throughout the course of treatment. Here, in the non-limiting Examples, the inventors present the first blood-based molecular biomarker data from CALGB 80405. These analyses utilized plasma samples collected prior to treatment (baseline) from patients receiving either bevacizumab or cetuximab. The number of patients who participated in CALGB 80405 is unique for colorectal cancer and any biomarker identified in this population will be particularly promising for prospective validation.

VEGF-D and PlGF were identified as predictive biomarkers for predicting the responsiveness of a cancer to a VEGF-targeting agent. Vascular endothelial growth factor D (VEGF-D) is a growth factor implicated in a variety of biological processes and well-known in the art. Placental growth factor (PlGF) is also a protein that functions in a variety of biological processes and is well-known in the art.

In the non-limiting Examples, high PlGF levels were identified as predictive of lack progression free survival (PFS) benefit from bevacizumab (bevacizumab HR=1.50, 95% CI 1.10-2.06; cetuximab HR=0.94, 95% CI 0.71-1.25; interaction p-value=0.0298). High levels of VEGF-D were predictive of lack of PFS benefit from bevacizumab in patients treated with FOLFOX chemotherapy (FOLFOX/bevacizumab HR=1.70, 95% CI 1.19-2.42; FOLFOX/cetuximab HR=0.92, 95% CI 0.68-1.24; interaction p-value=0.0097). Additionally, the present inventors discovered that high plasma levels of Ang-2, CD-73, HGF, ICAM-1, IL-6, OPN, TIMP-1, TSP-2, VCAM-1, and VEGFR-3 were identified as prognostic of shorter PFS and overall survival (OS).

In one aspect of the present invention, methods of predicting responsiveness of a cancer in a subject to a cancer therapy including a VEGF targeting agent are provided. The methods may include obtaining a sample from the subject, determining an expression level of at least one biomarker selected from the group consisting of VEGF-D and PlGF in a sample from the subject, comparing the expression level of the biomarker in the sample to a reference level of the biomarker, and predicting the responsiveness of the cancer to treatment with the cancer therapy including a VEGF targeting agent. Optionally, the methods may further include administering a VEGF target agent and/or an anticancer agent to the subject. In some embodiments, the expression levels of both VEGF-D and PlGF in the sample from the subject are determined.

In some embodiments, high expression levels of VEGF-D in the sample as compared to the reference level are predictive of lack of responsiveness to a VEGF targeting agent. In some embodiments, the prediction favors lack of responsiveness to a cancer therapy including a VEGF targeting agent when the expression level of VEGF-D is more than 0.1, 1.0, 1.1, 2, 3, 5, 7, 9, or 11 ng/mL in a plasma sample from the subject.

In some embodiments, high expression levels of PlGF in the sample as compared to the reference level are predictive of lack of responsiveness to a VEGF targeting agent. In some embodiments, the prediction favors lack of responsiveness to a cancer therapy including a VEGF targeting agent when the expression level of PlGF is more than 5, 10, 15, 15.3, 16, 17, 18, 20, 30, or 40 pg/mL in a plasma sample from the subject.

As used herein, a "sample" may or may not include cells. In particular, the methods described herein may be performed without requiring a tissue sample or biopsy and need not contain any cancer cells. In the Examples, plasma was used. A "sample" is intended to include any sampling of cells, tissues, or bodily fluids in which expression of a biomarker can be detected. Examples of such samples include, without limitation, biopsies, smears, blood, lymph, urine, saliva, or any other bodily secretion or derivative thereof. Blood may include whole blood, plasma (citrate, EDTA, heparin), serum, or any derivative of blood. Samples may be obtained from a subject by a variety of techniques available to those skilled in the art. Methods for collecting various samples are well known in the art.

The terms "subject" and "patient" are used interchangeably herein and refer to both human and non-human animals. The term "non-human animals" of the disclosure includes all vertebrates, e.g., mammals and non-mammals, such as non-human primates, sheep, dog, cat, horse, cow, chickens, amphibians, reptiles, and the like. Preferably, the subject is a human patient. More preferably, the subject is a human patient diagnosed with cancer or undergoing, or about to undergo or has undergone, a cancer therapy regimen. In some embodiments, the subject is KRAS wild-type.

As used herein, a "biomarker" is a polynucleotide or protein whose level of expression in a sample is indicative of a condition. In the Examples, the biomarkers are measured by assessing the expression levels of proteins encoded by genes. In some embodiments, the expression level of the biomarker is the protein expression level. In some embodiments, the expression level of the biomarker may be the mRNA expression level. These expression levels have, for example, been found to correlate with the sensitivity of a cancer to a VEGF targeting agent.

Fragments and variants of biomarker proteins and/or mRNA transcripts are also encompassed by the present invention. A "fragment" is intended to refer to a portion of the polynucleotide or a portion of the amino acid sequence and hence protein encoded thereby. Polynucleotides that are fragments of a biomarker nucleotide sequence generally comprise at least 10, 15, 20, 50, 75, 100, 150, 200, 250, 300, 350, 400, 450, 500, 550, 600, 650, 700, 800, 900, 1,000, 1,200, or 1,500 contiguous nucleotides, or up to the number of nucleotides present in a full-length biomarker polynucleotide disclosed herein. A fragment of a biomarker polypeptide will generally encode at least 15, 25, 30, 50, 100, 150, 200, or 250 contiguous amino acids, or up to the total number of amino acids present in a full-length biomarker protein of the invention. "Variant" is intended to mean substantially similar sequences. Generally, variants of a particular biomarker of the invention will have at least about 40%, 45%, 50%, 55%, 60%, 65%, 70%, 75%, 80%, 85%, 90%, 91%, 92%, 93%, 94%, 95%, 96%, 97%, 98%, 99% or more sequence identity to that biomarker as determined by sequence alignment programs.

Any methods available in the art for detecting expression of biomarkers are encompassed herein. The expression of a biomarker of the invention can be detected on a protein level or a nucleic acid level (e.g., as an mRNA transcript). "Measuring the expression level" means determining the quantity or presence of a protein or its RNA transcript for at least one of the biomarkers disclosed herein. Thus, "measuring the expression level" encompasses instances where a biomarker is determined not to be expressed, not to be detectably expressed, expressed at a low level, expressed at a normal level, or overexpressed. The expression level may be measured relative to a reference level of the biomarker.

Methods suitable for measuring, detecting, or determining the expression levels of biomarkers are known to those of skill in the art and include, but are not limited to, ELISA, immunofluorescence, FACS analysis, Western blot, magnetic immunoassays, and both antibody-based microarrays and non-antibody-based microarrays. In the past, the gold standard for detection of growth factors and cytokines in blood was the use of ELISAs; however, multiplex technology offers an attractive alternative approach for cytokine and growth factor analysis. The advantages of multiplex technology compared to traditional ELISA assays are conservation of patient sample, increased sensitivity, and significant savings in cost, time and labor.

Several multiplex platforms currently exist. The Luminex bead-based systems are the most established, being used to detect circulating cytokines and growth factors in both mice and humans. This method is based on the use of microparticles that have been pre-coated with specific antibodies. These particles are then mixed with sample and the captured analytes are detected using specific secondary antibodies. This allows for up to 100 different analytes to be measured simultaneously in a single microplate well. The advantages of this flow cytometry-based method compared to traditional ELISA assays are in the conservation of patient samples as well as significant savings in terms of cost and labor. An alternative, plate-based system is produced by Meso Scale Discovery (MSD). This system utilizes its proprietary Multi-Array® and Multi-Spot® microplates with electrodes directly integrated into the plates. This enables the MSD system to have ultra-sensitive detection limits, high specificity, and low background signal. Another plate-based multiplex system is the SearchLight Plus CCD Imaging System produced by Aushon Biosystems. The CiraScan Technology is yet another method of multiplex detection system. This novel multiplexing technology allows for the measurement of up to 10 different analytes simultaneously in a single microplate well. The assay design is similar to a sandwich ELISA where the capture antibodies are pre-spotted into individual wells of a 96-well plate. Samples or standards are added which bind to the specific capture antibodies and are detected using Aushon's patented SuperSignal ELISA Femto Chemiluminescent Substrate.

Methods for detecting expression of the biomarkers described herein are not limited to protein expression. Gene expression profiling including methods based on hybridization analysis of polynucleotides, methods based on sequencing of polynucleotides, immunohistochemistry methods, and proteomics-based methods may also be used. The most commonly used methods known in the art for the quantification of mRNA expression in a sample include northern blotting and in situ hybridization (Parker and Barnes, Methods Mol. Biol. 106:247-83, 1999), RNAse protection assays (Hod, Biotechniques 13:852-54, 1992), PCR-based methods, such as reverse transcription PCR(RT-PCR) (Weis et al., TIG 8:263-64, 1992), including real time quantitative PCR and array-based methods (Schena et al., Science 270:467-70, 1995). Alternatively, antibodies may be employed that can recognize specific duplexes, including DNA duplexes, RNA duplexes, and DNA-RNA hybrid duplexes, or DNA-protein duplexes. Representative methods for sequencing-based gene expression analysis include Serial Analysis of Gene Expression (SAGE) and gene expression analysis by massively parallel signature sequencing.

In the methods described herein the expression level of at least one biomarker described herein in a sample from the subject is determined using any one of the detection methods described herein. Then the level in the sample from the subject is compared to a reference level of the biomarker or a control. The "reference level" may be determined empirically by comparison to the levels found in a set of samples from cancer patients treated as described with known clinical outcomes for the patients. Alternatively, the reference level may be a level of the biomarker found in samples, such as plasma samples from the same subject, which becomes a standard and can be used as a predictor for new samples.

As used herein the term "predicting responsiveness" refers to providing a probability based analysis of how a particular subject will respond to a cancer therapy. A response to a cancer therapy includes any response including tumor shrinkage, slowing of growth, control of growth, increased, lengthened survival or any other measure showing treatment of the cancer. The prediction of responsiveness is not a guarantee or absolute, only a statistically probable indication of the responsiveness of the subject. The prediction of responsiveness to a cancer therapy including a VEGF targeting agent may indicate that the subject is likely to be responsive to a cancer therapy including a VEGF targeting agent or alternatively may indicate that the subject is not likely to be responsive to a cancer therapy including a VEGF targeting agent. Alternatively, the prediction may indicate that inclusion of a VEGF targeting agent in a cancer therapy regime may be counter-productive and lead to a worse result for the subject than if no therapy was used or a placebo was used or if the subject was treated with an alternative cancer treatment such as an EGFR targeting agent (i.e., cetuximab) or other chemotherapeutic or anti-cancer agent. Responsiveness includes, without limitation, any measure of a likelihood of clinical benefit. For example, clinical benefits include an increase in overall survival, an increase in progression free survival, an increase in time to progression, increased tumor response, decreased symptoms, or other quality of life benefits.

As used herein, a "VEGF targeting agent" includes any therapeutic agent targeting VEGF family members or any member of the VEGF receptor class of proteins. In particular, antibodies specific for VEGF, particularly VEGF-A, antibody-conjugated or other bioreagents capable of blocking VEGF mediated signaling, such as VEGF-R binding or competitive inhibitors, small molecules, aptamers, siRNAs, and other non-antibody-based therapeutic reagents. Anti-VEGF agents that are currently FDA approved include bevacizumab (Avastin™), sunitinib (Sutent™) sorafenib (Nexavar™), pazopanib (Votrient™), ranibizumab (Lucentis™), pegaptanib (Macugen™), Ramucirumab (Cyramza™), ziv-aflibercept (Zaltrap™), Regorafenib and Axitinib (Inlyte™). Bevacizumab is a monoclonal antibody against VEGF that is FDA approved for the treatment of metastatic colorectal cancer, lung cancer, renal cell cancer, and glioblastoma. Sunitinib is a small molecule tyrosine kinase inhibitor that blocks VEGF, PDGF, and cKIT receptors; sunitinib is FDA approved for the treatment of renal cell carcinoma and GI Stromal tumors (GIST). Sorafenib is a small molecule tyrosine kinase inhibitor that blocks VEGF, PDGF, and cKIT receptors as well as the oncogene Raf; sorafenib is FDA approved for the treatment of renal cell carcinoma and hepatocellular carcinoma. Pazopanib (Votrient™) is a small molecule tyrosine kinase inhibitor that blocks VEGF, PDGF, and cKIT receptors; pazopanib is FDA approved for the treatment of renal cell carcinoma. Ranibizumab (Lucentis™) is a Fab fragment antibody that binds VEGF; ranibizumab is FDA approved for the treatment neovascular (wet) age related macular degeneration (AMD). Pegaptanib (Macugen™) is a pegylated RNA aptamer that FDA approved for the treatment neovascular (wet) age related macular degeneration (AMD). Axitinib (Inlyte™) is a small molecule tyrosine kinase inhibitor capable of inhibiting VEGFR1, VEGFR2, VEGFR3, PDGFR and cKIT that is FDA approved for treatment of renal cell carcinoma. Multiple other VEGF and other angiogenesis inhibitors are in various stages of clinical development.

The VEGF targeting agents may be used in combination with other cancer therapeutics in a cancer therapy regimen. Combination therapy does not require that multiple cancer therapeutics be administered simultaneously, but only that the subjects are treated with more than one therapeutic agent during a time span, such as one month, two months or more. For example, the VEGF targeting agent may be used in combination with an anticancer agent. As used herein, a "an anticancer agent" or "chemotherapy agent" may include compounds that may be used to treat cancer. Suitable anticancer or chemotherapy agents may include, without limitation, 5-fluorouracil, aclacinomycin, activated cytoxan, bisantrene, bleomycin, carmofur, CCNU, cis-platinum, daunorubicin, doxorubicin, DTIC, melphalan, methotrexate, mithromycin, mitomycin, mitomycin C, peplomycin pipobroman, plicamycin, procarbazine, retinoic acid, tamoxifen, taxol, tegafur, VP16, or VM25. In some embodiments, the anticancer agent may be FOLFOX or FOLFIRI. FOLFOX is a chemotherapy regimen made up of the drugs folinic acid (leucovorin), fluorouracil (5-FU), and oxaliplatin. FOLFIRI is a chemotherapy regimen made up of the drugs folinic acid (leucovorin), fluorouracil (5-FU), and irinotecan.

As used herein, a "cancer" may be selected from any cancer in which a VEGF targeting agent is being considered for therapeutic purposes. In particular, the cancer may be a solid tumor. Cancers for which predictions may be made include, without limitation, colorectal, pancreatic, liver, esophageal, gastric, small bowel, cholangiocarcinoma, lung, head and neck, thyroid, melanoma, breast, renal, bladder, ovarian, uterine, prostate, lymphomas, leukemias, sarcoma, neuroendocrine, glioblastoma or any other form of brain tumor. Suitably, the cancer is colorectal cancer.

In another aspect, the present invention relates to methods of developing a prognosis for a subject diagnosed with a cancer. The methods may include determining an expression level of at least one biomarker selected from the group consisting of Angiopoietin-2 (Ang-2), Cluster of Differentiation 73 (CD-73 or NTSE), Hepatocyte growth factor (HGF), Intercellular adhesion molecule 1 (ICAM-1), Interleukin 6 (IL-6), Osteopontin (OPN), TIMP metallopeptidase inhibitor 1 (TIMP-1), Thrombospondin-2 (TSP-2), Vascular cell adhesion molecule 1 (VCAM-1), and Vascular endothelial growth factor receptor 3 (VEGFR-3) in a sample from the subject, comparing the expression levels of the at least one biomarker in the sample to reference levels, and determining a survival or outcome prognosis for the subject. The subject may or may not be being treated with a VEGF-targeting agent or an EGFR targeting agent.

As used herein, an "EGFR targeting agent" includes any therapeutic agent targeting any member of the EGFR family of proteins. In particular, antibodies specific for EGFR or other bioreagents capable of affecting EGFR mediated signaling, such as EGFR binding or competitive inhibitors, small molecules, aptamers, iRNAs, siRNAs, microRNAs, and other non-antibody-based therapeutic reagents. EGFR targeting agents include, without limitation, cetuximab (Erbitux™), gefitinib (Iressa™), erlotinib (Tarceva™), afatinib (GilotrifrM), brigatinib, panitumumab (Vectibix) and icotinib. Cetuximab is a monoclonal antibody against EGFR that is FDA approved for the treatment of head and neck cancer and colorectal cancer in patients whose tumors have a KRAS-wildtype gene. Gefitinib, Erlotinib, Afatinib, Brigatinib, and Icotinib are all small molecule inhibitors of EGFR each used to treat certain types of cancer. Multiple other EGFR targeting agents are in various stages of clinical development. Suitably, the EGFR targeting agent is cetuximab. In some embodiments, high expression levels of the at least one biomarker in the sample as compared to the reference level are indicative of a poor survival or outcome prognosis.

In some embodiments, a poor survival or outcome prognosis is determined when the expression level of Ang-2 is more than 90, 100, 116.2, 120, or 150 pg/mL, CD-73 is more than 2, 3, 4.6, 8, 10, 20, or 30 pg/mL, HGF is more than 100, 200, 376.1, 400, or 500 pg/mL, ICAM-1 is more than 400, 500, 621.4, 700, or 800 ng/mL, IL-6 is more than 10, 20, 28.6, 40 or 50 pg/mL, OPN is more than 700, 800, 968.2, 1100 or 1200 ng/mL, TIMP-1 is more than 100, 175.3, 200, or 300 ng/mL, TSP-2 is more than 90, 100, 114.7, 200, or 300 ng/mL, VCAM-1 is more than 1, 2, 3, or 4 µg/mL, and/or VEGFR-3 is more than 100, 200, 276.8, 300, or 400 ng/mL in a plasma sample from the subject.

In a further aspect, methods are provided. The methods may include obtaining a sample from the subject, and determining an expression level of at least one, two, three, four, five, six, seven, eight, nine, ten, eleven, or twelve biomarker(s) selected from the group consisting of VEGF-D, PlGF, Ang-2, CD-73, HGF, ICAM-1, IL-6, OPN, TIMP-1, TSP-2, VCAM-1, and VEGFR-3 in a sample from the subject. In some embodiments, the expression levels of both VEGF-D and PlGF in the sample from the subject are determined. In some embodiments, the expression levels of at least three, four, five, six or all of the biomarkers in the sample from the subject are determined. Determination of the expression level of more than one biomarker will increase the likelihood or strength of the prediction of responsiveness to the therapeutic including a VEGF targeting agent or the prognosis.

Methods of treating cancer in a subject are provided. The methods may include administering to the subject a therapeutically effective amount of a VEGF targeting agent based on an expression level of VEGF-D, PlGF, or both in a sample from the subject. Optionally, the methods may further include administering an anticancer or chemotherapy agent to the subject. In some embodiments, low levels of expression of the biomarker are indicative of responsiveness to the VEGF targeting agent. In some embodiments, the subject is administered the VEGF targeting agent if the expression level of VEGF-D is less than 0.1, 1.1, 3, 5, 7, 9, or 11 ng/mL in a plasma sample from the subject. In some embodiments, the subject is administered the VEGF targeting agent if the expression level of PlGF is less than 5, 10, 15.3, 20, 30, or 40 pg/mL in a plasma sample from the subject.

"Treating cancer" includes, without limitation, reducing the number of cancer cells or the size of a tumor in the subject, reducing progression of a cancer to a more aggressive form (i.e. maintaining the cancer in a form that is susceptible to a therapeutic agent), reducing proliferation of cancer cells or reducing the speed of tumor growth, killing of cancer cells, reducing metastasis of cancer cells or reducing the likelihood of recurrence of a cancer in a subject. Treating a subject as used herein refers to any type of treatment that imparts a benefit to a subject afflicted with cancer or at risk of developing cancer or facing a cancer recurrence. Treatment includes improvement in the condition of the subject (e.g., in one or more symptoms), delay in the progression of the disease, delay in the onset of symptoms or slowing the progression of symptoms, increase in progression free survival, overall survival etc.

As used herein, an "effective amount" or a "therapeutically effective amount" as used herein means the amount of a composition that, when administered to a subject for treating a state, disorder or condition is sufficient to effect a treatment (as defined above). The therapeutically effective amount will vary depending on the compound, formulation or composition, the disease and its severity and the age, weight, physical condition and responsiveness of the subject to be treated.

The VEGF targeting agent described herein may be administered by any means known to those skilled in the art, including, without limitation, intravenously, intra-tumoral, intra-lesional, intradermal, topical, intraperitoneal, intramuscular, parenteral, subcutaneous and topical administration Thus the compositions may be formulated as an injectable, topical, ingestible, or suppository formulation. Administration of the VEGF targeting agent to a subject in accordance with the present invention may exhibit beneficial effects in a dose-dependent manner. Thus, within broad limits, administration of larger quantities of the compositions is expected to achieve increased beneficial biological effects than administration of a smaller amount. Moreover, efficacy is also contemplated at dosages below the level at which toxicity is seen.

It will be appreciated that the specific dosage of the VEGF targeting agent administered in any given case will be adjusted in accordance with the composition or compositions being administered, the volume of the composition that can be effectively delivered to the site of administration, the disease to be treated or inhibited, the condition of the subject, and other relevant medical factors that may modify the activity of the compositions or the response of the subject, as is well known by those skilled in the art. For example, the specific dose of a VEGF targeting agent for a particular subject depends on age, body weight, general state of health, diet, the timing and mode of administration, the rate of excretion, medicaments used in combination and the severity of the particular disorder to which the therapy is applied. Dosages for a given patient can be determined using conventional considerations, e.g., by customary comparison of the differential activities of the compositions described herein and of a known agent, such as by means of an appropriate conventional pharmacological protocol. The compositions can be given in a single dose schedule, or in a multiple dose schedule.

The maximal dosage of a VEGF targeting agent for a subject is the highest dosage that does not cause undesirable or intolerable side effects. The number of variables in regard to an individual treatment regimen is large, and a considerable range of doses is expected. The route of administration will also impact the dosage requirements. It is anticipated that dosages of the compositions will treat cancer, for example, by reducing tumor size or decreasing the rate of tumor growth by least 10%, 20%, 30%, 40%, 50%, 60%, 70%, 80%, 90%, 100% or more as compared to no treatment.

The effective dosage amounts of a VEGF targeting agent refer to total amounts administered, that is, if more than one composition is administered, the effective dosage amounts of a VEGF targeting agent corresponds to the total amount administered. The compositions can be administered as a single dose or as divided doses. For example, the composition may be administered two or more times separated by 4 hours, 6 hours, 8 hours, 12 hours, a day, two days, three days, four days, one week, two weeks, or by three or more weeks.

Suitable dosage ranges for a VEGF targeting agent may be of the order of several hundred micrograms of the agent with a range from about 0.001 to 10 mg/kg/day, preferably in the range from about 0.01 to 1 mg/kg/day. Precise amounts of a VEGF targeting agent required to be administered depend on the judgment of the practitioner and may be peculiar to each subject. It will be apparent to those of skill in the art that the therapeutically effective amount of the compositions and pharmaceutical compositions described herein will depend, inter alia, upon the administration schedule, the unit dose of agent administered, whether the composition is administered in combination with other therapeutic agents, the status and health of the recipient, and the therapeutic activity of the particular composition.

The present disclosure is not limited to the specific details of construction, arrangement of components, or method steps set forth herein. The compositions and methods disclosed herein are capable of being made, practiced, used, carried out and/or formed in various ways that will be apparent to one of skill in the art in light of the disclosure that follows. The phraseology and terminology used herein is for the purpose of description only and should not be regarded as limiting to the scope of the claims. Ordinal indicators, such as first, second, and third, as used in the description and the claims to refer to various structures or method steps, are not meant to be construed to indicate any specific structures or steps, or any particular order or configuration to such structures or steps. All methods described herein can be performed in any suitable order unless otherwise indicated herein or otherwise clearly contradicted by context. The use of any and all examples, or exemplary language (e.g., "such as") provided herein, is intended merely to facilitate the disclosure and does not imply any limitation on the scope of the disclosure unless otherwise claimed. No language in the specification, and no structures shown in the drawings, should be construed as indicating that any non-claimed element is essential to the practice of the disclosed subject matter. The use herein of the terms "including," "comprising," or "having," and variations thereof, is meant to encompass the elements listed thereafter and equivalents thereof, as well as additional elements. Embodiments recited as "including," "comprising," or "having" certain elements are also contemplated as "consisting essentially of" and "consisting of" those certain elements.

Recitation of ranges of values herein are merely intended to serve as a shorthand method of referring individually to each separate value falling within the range, unless otherwise indicated herein, and each separate value is incorporated into the specification as if it were individually recited herein. For example, if a concentration range is stated as 1% to 50%, it is intended that values such as 2% to 40%, 10% to 30%, or 1% to 3%, etc., are expressly enumerated in this specification. These are only examples of what is specifically intended, and all possible combinations of numerical values between and including the lowest value and the highest value enumerated are to be considered to be expressly stated in this disclosure. Use of the word "about" to describe a particular recited amount or range of amounts is meant to indicate that values very near to the recited amount are included in that amount, such as values that could or naturally would be accounted for due to manufacturing tolerances, instrument and human error in forming measurements, and the like. All percentages referring to amounts are by weight unless indicated otherwise.

No admission is made that any reference, including any non-patent or patent document cited in this specification, constitutes prior art. In particular, it will be understood that, unless otherwise stated, reference to any document herein does not constitute an admission that any of these documents forms part of the common general knowledge in the art in the United States or in any other country. Any discussion of the references states what their authors assert, and the applicant reserves the right to challenge the accuracy and pertinence of any of the documents cited herein. All references cited herein are fully incorporated by reference in their entirety, unless explicitly indicated otherwise. The present disclosure shall control in the event there are any disparities between any definitions and/or description found in the cited references.

Unless otherwise specified or indicated by context, the terms "a", "an", and "the" mean "one or more." For example, "a protein" or "an RNA" should be interpreted to mean "one or more proteins" or "one or more RNAs," respectively.

The following examples are meant only to be illustrative and are not meant as limitations on the scope of the invention or of the appended claims.

EXAMPLES

Example 1—Plasma Protein Biomarkers Predictive of Benefit from Bevacizumab Versus Cetuximab in Colorectal Cancer: Results from CALGB 80405 (Alliance)

Purpose:

CALGB 80405 was the largest trial to date evaluating the anti-vascular endothelial growth factor A (VEGF-A) agent bevacizumab and the anti-epidermal growth factor receptor (EGFR) agent cetuximab in the treatment of metastatic colorectal cancer. Progression-free survival (PFS) and overall survival (OS) were similar between the two agents. Biomarkers that can predict which patients benefit from each of these biological agents are urgently needed.

Patients and Methods:

Levels of 23 soluble proteins were measured using multiplex ELISA technology in baseline plasma samples collected from KRAS wild-type patients participating in CALGB 80405. Prognostic markers were determined using univariate Cox proportional hazards models independent of treatment arm. Predictive markers were identified using multivariate Cox regression models including interaction between marker level and treatment.

Results:

High plasma levels of Ang-2, CD-73, HGF, ICAM-1, IL-6, OPN, TIMP-1, TSP-2, VCAM-1, and VEGFR-3 were identified as prognostic of shorter PFS and OS. PlGF was identified as predictive of lack PFS benefit from bevacizumab (bevacizumab HR=1.50, 95% CI 1.10-2.06; cetuximab HR=0.94, 95% CI 0.71-1.25; interaction p-value=0.0298). High levels of VEGF-D were predictive of lack of PFS benefit from bevacizumab in patients treated with FOLFOX chemotherapy (FOLFOX/bevacizumab HR=1.70, 95% CI 1.19-2.42; FOLFOX/cetuximab HR=0.92, 95% CI 0.68-1.24; interaction p-value=0.0097).

Conclusions:

PlGF and VEGF-D were identified as potential predictive markers for bevacizumab in CALGB 80405. The consistency of the VEGF-D finding in this and other studies suggests it may be a candidate for prospective validation as a predictive molecular biomarker of bevacizumab efficacy.

Methods:

Study Design and Patients

Figure 1:
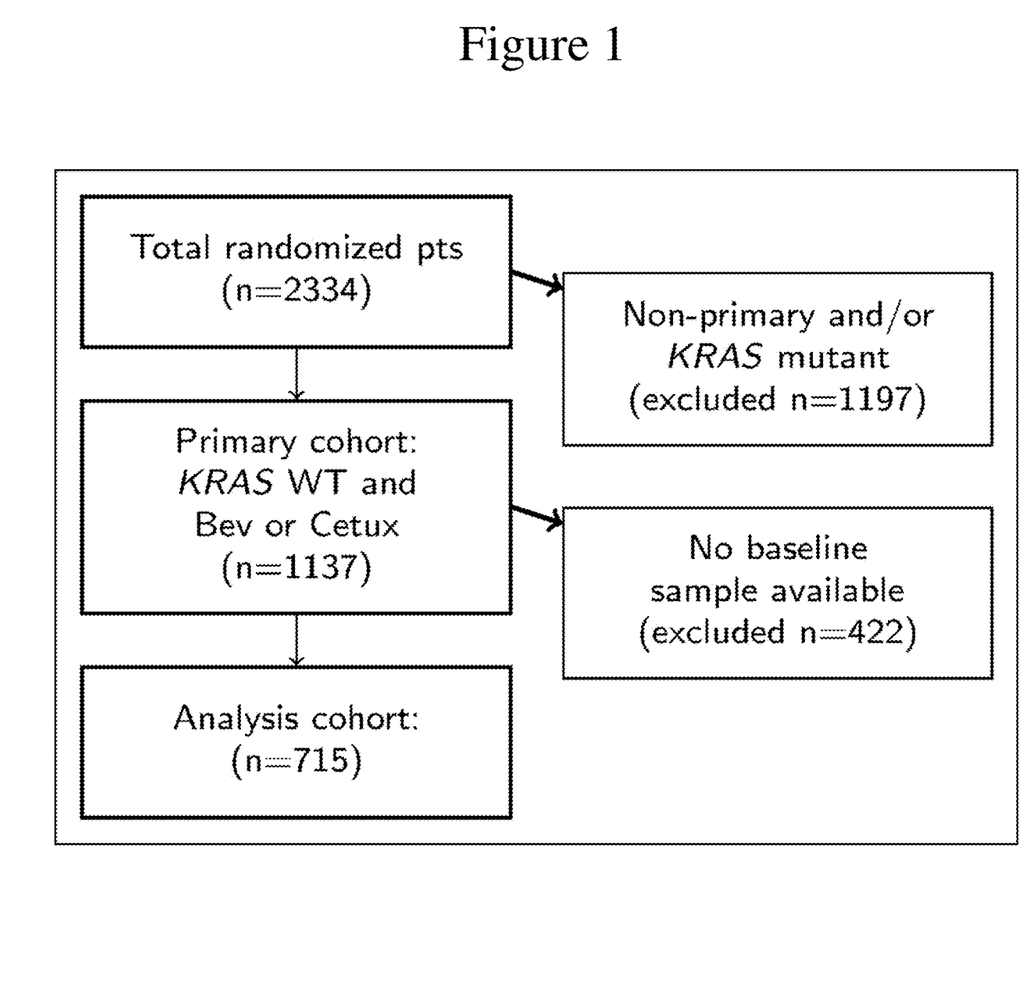
FIG. 1 shows a sample flowchart.

The study design of CALGB 80405 and clinical results were reported previously. See Venook, A. P., et al., *CALGB/SWOG 80405: Phase III trial of irinotecan/5-FU/leucovorin (FOLFIRI) or oxaliplatin/5-FU/leucovorin (mFOLFOX6) with bevacizumab (BV) or cetuximab (CET) for patients (pts) with KRAS wild-type (wt) untreated metastatic adenocarcinoma of the colon or rectum (MCRC)*. J Clin Oncol, 2014. 32: p. suppl; abstr LBA3. Briefly, patients with locally advanced or metastatic colorectal cancer (CRC) were randomized to receive either bevacizumab, cetuximab, or the combination in conjunction with chemotherapy (FOLFOX or FOLFIRI at the discretion of the treating physician). The study was later amended to stop enrollment in the combination arm and to implement KRAS mutation testing. The samples used in the described analyses were collected from only KRAS wild-type patients randomized to the bevacizumab or cetuximab arm of CALGB 80405. A patient consort diagram is shown in FIG. 1.

Sample Collection

Peripheral venous blood was collected at baseline from consenting patients into vacutainers containing EDTA anticoagulant. Samples were centrifuged at 2500×g for 15 min within 30 min of collection. The resulting plasma was spun again at 2500×g for 15 min. Double-spun plasma was aliquoted, frozen, and shipped to The Alliance Pathology Coordinating Office for centralized storage. Prior to analyses, samples were thawed on ice, realiquoted, and stored at −80° C.

Protein Analysis

Levels of 23 soluble proteins (Table 3) were measured in plasma using multiplex enzyme-linked immunosorbent assay (ELISA) techniques on the Aushon Biosystems (Billerica, Mass.) and MesoScale Discovery (Rockville, Md.) platforms as previously described.

Statistical Analysis

All marker levels were log-transformed before analysis. All analyses were performed using baseline data from all available patients with continuous values for the protein analytes. Markers prognostic of clinical outcome (OS or PFS), were determined using univariate Cox proportional hazards models independent of treatment arm, and the resulting hazard ratios (HR), 95% confidence intervals (CI), and p-values are reported. Multivariate Cox regression models were used to test for interaction between marker level and treatment arm to identify markers predictive of benefit from bevacizumab or cetuximab. For VEGF-D predictive analyses treatment arm was stratified by type of chemotherapy (FOLFOX or FOLFIRI). P-values were not adjusted for multiple testing.

Forest plots were created to depict prognostic effect sizes (HRs and corresponding 95% CIs). VEGF-D levels were dichotomized at the first quartile as "high" or "low", and Kaplan-Meier plots of OS or PFS were created with separate curves for each combination of treatment group and marker level. The Alliance Statistics and Data Center conducted data collection and statistical analyses, and the clinical data were locked as of Dec. 15, 2015. The R software environment for statistical computing and graphics and the survival package were used to execute the statistical analyses and to generate the figures.

Results:

Patient Characteristics

The demographic and survival characteristics of the study population are shown in Table 1. All of the patients included in this study are KRAS wild-type at codons 12 and 13 and were randomized to the bevacizumab or cetuximab arm of CALGB 80405. The characteristics of the biomarker study population are similar to those of the non-biomarker population and the overall study population. See Table 2. Samples were analyzed from 715 of the 1137 patients in the primary cohort. The baseline characteristics of all 23 biomarkers evaluated are shown in Table 3.

TABLE 1

Comparison of biomarker subpopulations and the overall patient population.

|  | N | No Baseline Plasma 422 | Baseline Plasma 715 | Overall Pts 1137 |
|---|---|---|---|---|
| AGE | Median (range) | 59 (20-89) | 59 (21-84) | 59 (20-89) |
| RACE | African American | 57 (13.5%) | 72 (10.1%) | 129 (11.3%) |
|  | Asian | 16 (3.8%) | 19 (2.7%) | 35 (3.1%) |
|  | Caucasian | 323 (76.5%) | 611 (85.5%) | 934 (82.1%) |
|  | Multiple | 4 (0.9%) | 1 (0.1%) | 5 (0.4%) |
|  | Other | 22 (5.2%) | 12 (1.7%) | 34 (3.0) |
| GENDER | Female | 168 (39.8%) | 272 (38.0%) | 440 (38.7%) |
|  | Male | 254 (60.2%) | 443 (62.0%) | 697 (61.3%) |
| MEDIAN OUTCOME (months) | OS (95% CI) | 26.1 (23.7-30.0) | 31.0 (29.0-33.0) | 29.4 (27.6-31.4) |
|  | PFS (95% CI) | 9.9 (9.3-11.3) | 10.9 (10.1-11.3) | 10.6 (9.8-11.1) |

TABLE 2

Biomarker subpopulations across different chemotherapy treatment groups.

|  | N | FOLFIRI/ Bev 98 | FOLFOX/ Bev 259 | FOLFIRI/ Cetux 94 | FOLFOX/ Cetux 264 |
|---|---|---|---|---|---|
| AGE | Median (range) | 61 (33-81) | 58 (21-83) | 59 (36-83) | 59 (22-84) |
| RACE | African American | 9 (9.2%) | 22 (8.5%) | 10 (10.6%) | 31 (11.7%) |
|  | Asian | 4 (4.1%) | 4 (1.5%) | 2 (2.1%) | 9 (3.4%) |
|  | Caucasian | 84 (85.7%) | 228 (88.0%) | 81 (86.2%) | 218 (82.6%) |
|  | Multiple | 0 (0.0%) | 0 (0.0%) | 0 (0.0%) | 1 (0.4%) |
|  | Other | 1 (1.0%) | 5 (1.9%) | 1 (1.1%) | 5 (1.9%) |
| GENDER | Female | 37 (37.8%) | 95 (36.7%) | 37 (39.4%) | 103 (39.0%) |
|  | Male | 61 (62.2%) | 164 (63.3%) | 57 (60.6%) | 161 (61.0%) |
| MEDIAN OUTCOME (months) | OS (95% CI) | 35.1 (29.4-41.3) | 30.3 (27.1-33.2) | 31.9 (26.8-40.2) | 28.9 (25.3-34.6) |
|  | PFS (95% CI) | 12.4 (10.3-14.0) | 10.8 (9.5-11.7) | 10.9 (9.2-14.4) | 10.0 (9.2-11.3) |

TABLE 3

Biomarker baseline levels.

| Biomarker | Unit | Median | Range |
|---|---|---|---|
| Ang-2 | pg/ml | 116.2 | 0.3-1308 |
| BMP-9 | pg/ml | 183.1 | 36.3-197300 |
| CD73 | pg/ml | 4.6 | 0.6-2042 |
| HER-3 | pg/ml | 19.4 | 2.9-1141 |
| HGF | pg/ml | 376.1 | 5.7-106700 |
| ICAM-1 | ng/ml | 621.4 | 144.3-3398 |
| IL-6 | pg/ml | 28.6 | 1.9-3867 |
| OPN | ng/ml | 968.2 | 20.2-64110 |
| PDGF-AA | pg/ml | 737.2 | 0.7-12910 |
| PDGF-BB | pg/ml | 1267 | 16.5-16090 |
| PlGF | pg/ml | 15.3 | 2.5-328.2 |
| SDF-1 | ng/ml | 5.3 | 11.8-54 |
| TGF-β1 | ng/ml | 76.5 | 8.8-577.6 |
| TGF-β2 | pg/ml | 94.1 | 19.7-487.8 |
| TGFβ-R3 | ng/ml | 91.4 | 17.2-587.4 |
| TIMP-1 | ng/ml | 175.3 | 50.3-1537 |
| TSP-2 | ng/ml | 114.7 | 26.8-2322 |
| VCAM-1 | μg/ml | 2.0 | 0.7-11.1 |
| VEGF-A | pg/ml | 83.1 | 0.2-3332 |
| VEGF-D | ng/ml | 1.1 | 0.1-18.3 |
| VEGF-R1 | pg/ml | 195.3 | 4.2-14930 |
| VEGF-R2 | ng/ml | 3.9 | 0.9-16.5 |
| VEGF-R3 | ng/ml | 276.8 | 96.8-767 |

Prognostic Analyses

Figure 2A:
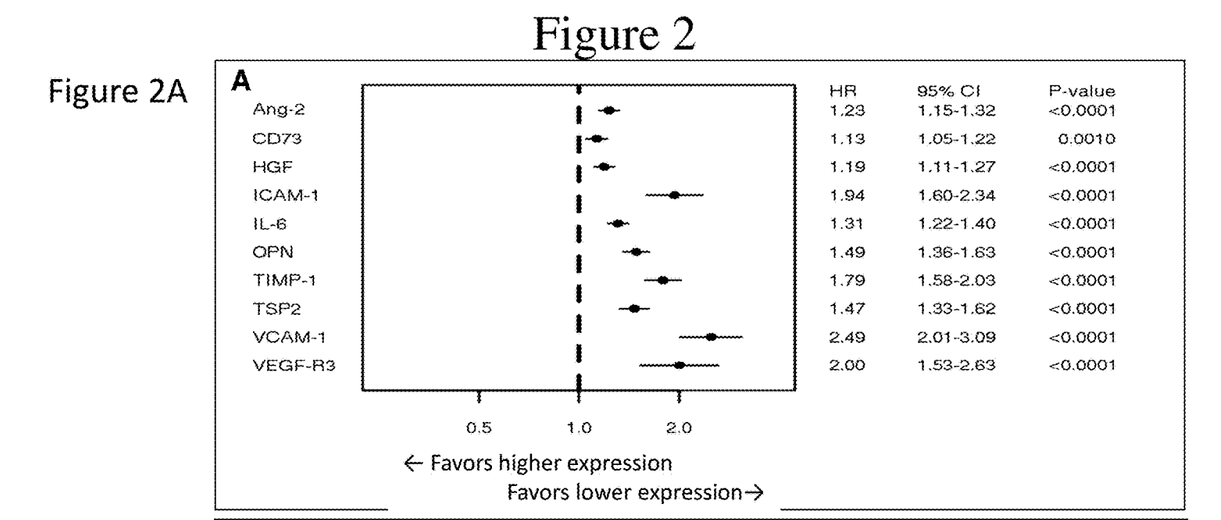
Figure 2B:
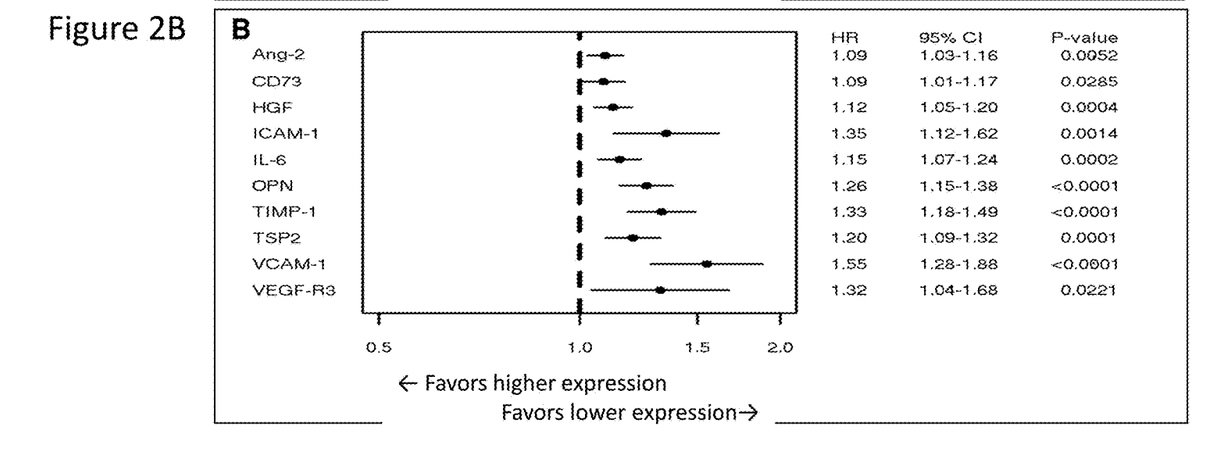

Ten markers (Ang-2, CD-73, HGF, ICAM-1, IL-6, OPN, TIMP-1, TSP-2, VCAM-1, and VEGFR-3) were prognostic for both PFS and OS. For every marker, higher expression was associated with shorter PFS or OS. Forest plots showing the prognostic associations of marker levels with PFS and OS are shown in FIG. 2. The largest prognostic effects in PFS (HR=1.55, 95% CI 1.28-1.88, p<0.0001) and OS (HR=2.49, 95% CI 2.01-3.09, p<0.0001) were observed for VCAM-1, a cell-surface protein that regulates the interactions between endothelial cells and various circulating immune cells. ICAM-1, a cell-surface protein with functions similar to those of VCAM-1, also had strong prognostic effects for PFS (HR=1.35, 95% CI 1.12-1.62, p=0.0014) and OS (HR=1.94, 95% CI 1.60-2.34, p<0.0001). OPN (PFS HR=1.26, 95% CI 1.15-1.38, p<0.0001; OS HR=1.49, 95% CI 1.36-1.63, p<0.0001), TIMP-1 (PFS HR=1.33, 95% CI 1.18-1.49, p<0.0001; OS HR=1.79, 95% CI 1.58-2.03, p<0.0001), and TSP-2 (PFS HR=1.20, 95% CI 1.09-1.32, p=0.0001; OS HR=1.47, 95% CI 1.33-1.62, p<0.0001) regulate interactions with and remodeling of the extracellular matrix important for angiogenesis. Ang-2 (PFS HR=1.09, 95% CI 1.03-1.16, p=0.0052; OS HR=1.23, 95% CI 1.15-1.32, p<0.0001), HGF (PFS HR=1.12, 95% CI 1.05-1.20, p=0.0004; OS HR=1.19, 95% CI 1.11-1.27, p<0.0001), and VEGFR-3 (PFS HR=1.32, 95% CI 1.04-1.68, p=0.0221; OS HR=2.00, 95% CI 1.53-2.63, p<0.0001) all have roles in regulating angiogenesis. CD-73 (PFS HR=1.09, 95% CI 1.01-1.17, p=0.0285; OS HR=1.13, 95% CI 1.05-1.22, p=0.0010) and IL-6 (PFS HR=1.15, 95% CI 1.07-1.24, p=0.0002; OS HR=1.31, 95% CI 1.22-1.40, p<0.0001) are associated with inflammatory and immune signaling.

Predictive Analyses

Figure 3:
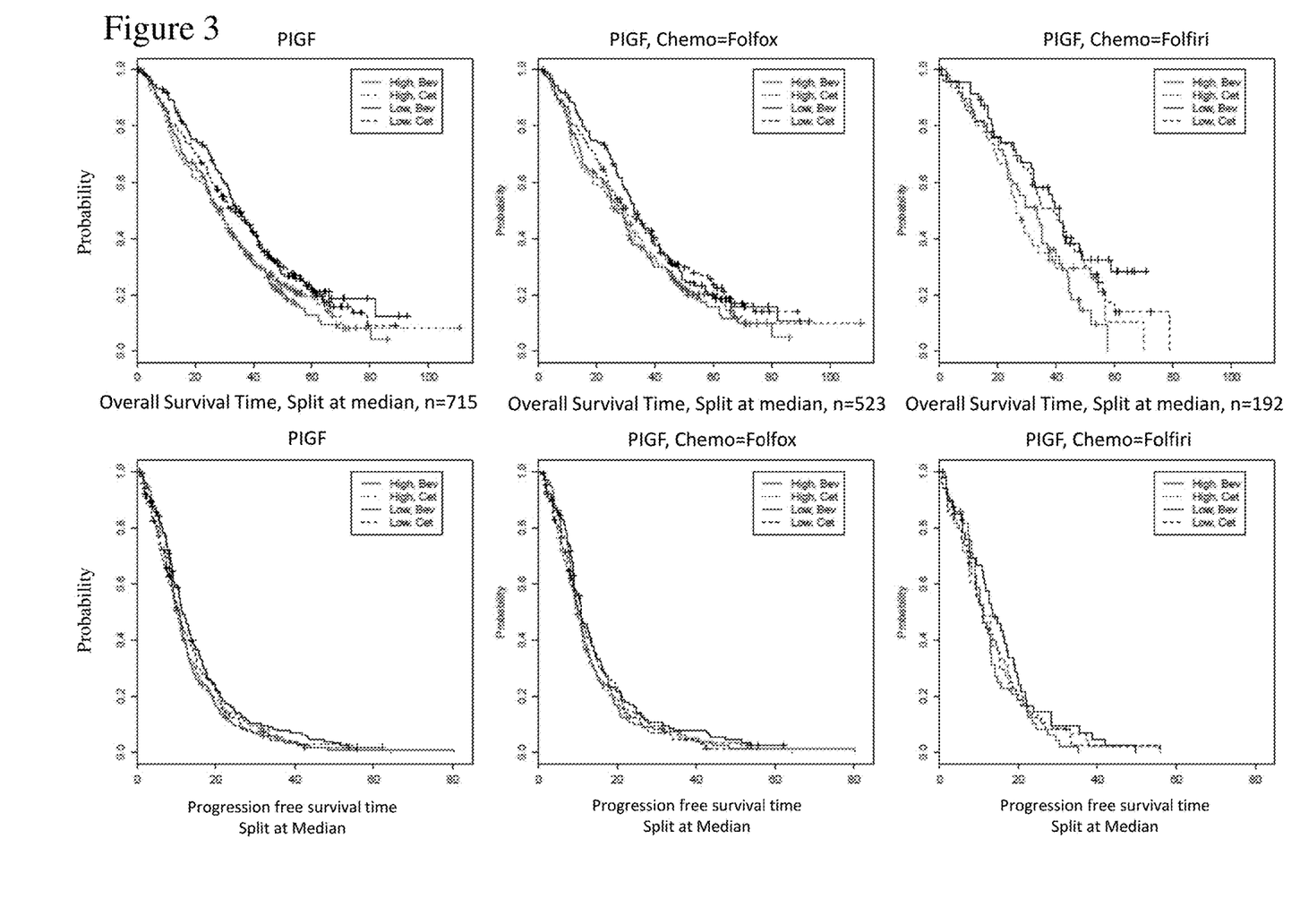
FIG. 3 shows Kaplan-Meier curves illustrating the predictive effect of PlGF protein level.

Higher PlGF protein levels were predictive of lack of PFS benefit from bevacizumab (bevacizumab HR=1.50, 95% CI 1.10-2.06; cetuximab HR=0.94, 95% CI 0.71-1.25; interaction p-value=0.0298) when patients were categorized by treatment arm independent of the chemotherapy administered. See Table 4. No other markers were predictive of survival outcome across all of the patients in this analysis. The PlGF effect appeared to be driven by increasing PFS hazard with increasing PlGF expression in patients treated with bevacizumab because no PlGF predictive effect was observed in the patients treated with cetuximab. A Kaplan-Meier curve illustrating the predictive effect of PlGF protein level is shown in FIG. 3.

Figure 4:
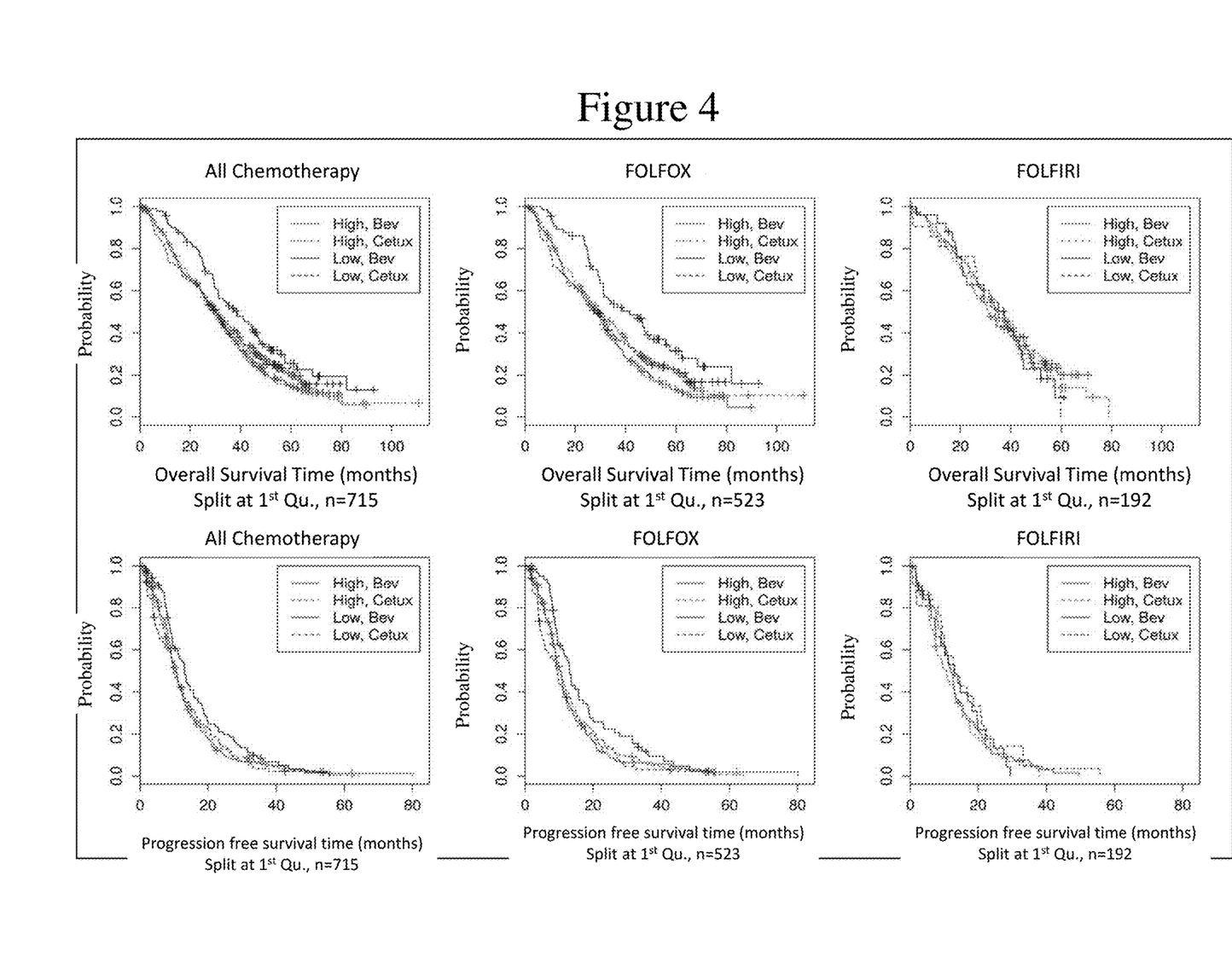
FIG. 4 shows VEGF-D Kaplan-Meier plots (dichotomized at the 1st quartile).
Figure 5A:
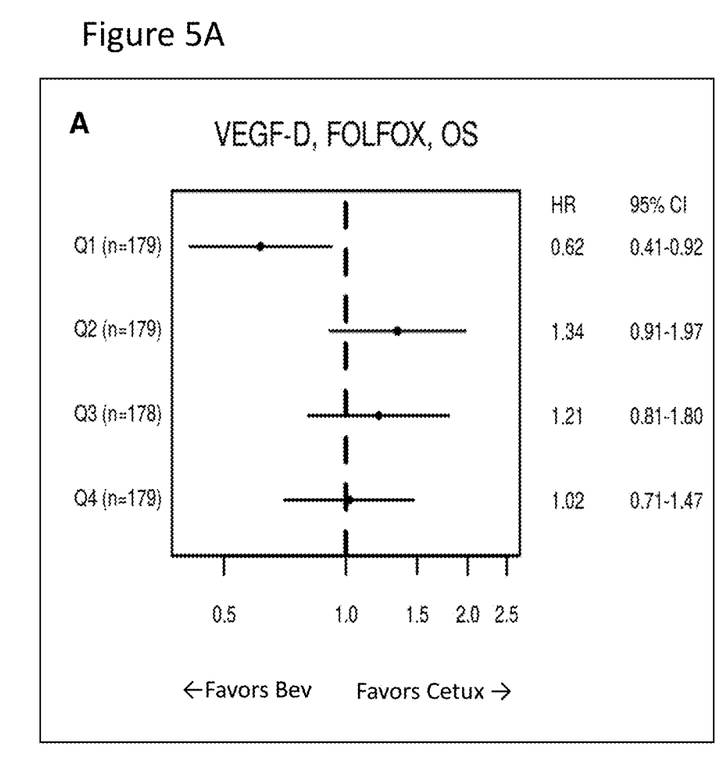
Figure 5B:
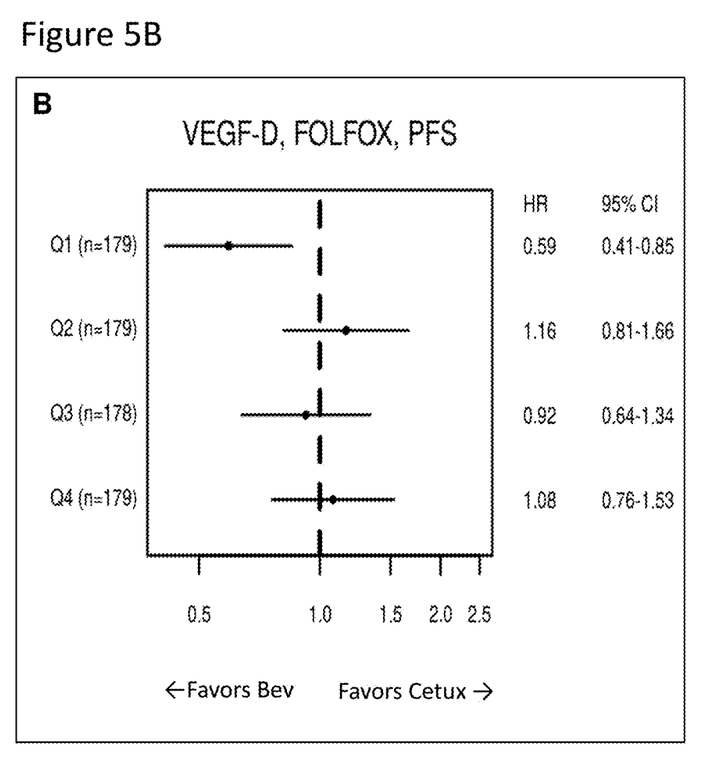

To control for the different chemotherapies used in CALGB 80405 the two groups were stratified by chemotherapy (FOLFOX or FOLFIRI) and all markers were re-analyzed for predictive associations. This analysis found VEGF-D to be predictive of lack of PFS benefit in patients receiving FOLFOX and bevacizumab (FOLFOX/bevacizumab HR=1.70, 95% CI 1.19-2.42; FOLFOX/cetuximab HR=0.92, 95% CI 0.68-1.24; interaction p-value=0.0097), but not in patients receiving FOLFIRI and bevacizumab (FOLFIRI/bevacizumab HR=0.95, 95% CI 0.61-1.48; FOLFIRI/cetuximab HR=1.37, 95% CI 0.73-2.56; interaction p-value=0.4336). See Table 4. This FOLFOX-related effect was not observed for OS (interaction p-value=0.1151). No other markers were predictive for PFS or OS when patients were stratified by chemotherapy. We have previously shown that low levels of VEGF-D protein (first quartile) are predictive of benefit from bevacizumab and gemcitabine in advanced pancreatic cancer (80303). To examine whether those previous findings were applicable in the context of CRC, forest plots were generated to illustrate the effects of VEGF-D protein levels on PFS (FIG. 5B) and OS (FIG. 5A) in patients receiving FOLFOX. Kaplan-Meier curves showing the effects of VEGF-D protein levels and chemotherapy are shown in FIG. 4. All groups in the Kaplan-Meier graphs are dichotomized at the first quartile of VEGF-D levels.

and unprecedented source of material for biomarker studies that may help guide the use of these critical therapeutics. CALGB 80405 showed that in KRAS wild-type patients, there are no significant PFS or OS differences between patients treated with bevacizumab or cetuximab. However, these agents have distinct mechanisms of action and toxicity profiles and biomarker information could provide important insight for clinical decision making. Recently, it was observed that the location of the primary CRC tumor, i.e., sidedness, is associated with prognosis and may be associated with benefit from either bevacizumab or cetuximab. Tumors on the left side of the colon were associated with longer PFS and OS and increased benefit from cetuximab versus bevacizumab. Another large, randomized phase III trial comparing bevacizumab and cetuximab (FIRE-3) showed that cetuximab provides a greater OS benefit than bevacizumab. However, there are important differences between FIRE-3 and CALGB 80405. In FIRE-3, the primary efficacy endpoint was objective response rather than survival, FOLFIRI was the only chemotherapy regimen used, and cetuximab was not associated with a PFS benefit relative to bevacizumab. The differences in outcomes between two similar phase III trials emphasizes the need to identify biomarkers that can clarify clinical decision making or prioritize pathways for additional investigation. Our analysis of 23 soluble protein biomarkers in plasma focused on targets that participate in angiogenic signaling, EGFR-pathway signaling, or had that had been previously implicated as potential predictive biomarkers for either bevacizumab or cetuximab.

PlGF and VEGF-D were identified as potential predictive markers of benefit from bevacizumab. Both PlGF and VEGF-D are ligands that bind and activate signaling through VEGFRs. Lower baseline levels of PlGF or VEGF-D at baseline indicate that these ligands are less able to initiate signaling that could bypass the effects of VEGF-A-depletion in the context of treatment with bevacizumab. PlGF was predictive of PFS benefit from bevacizumab (bevacizumab HR=1.50, 95% CI 1.10-2.06; cetuximab HR=0.94, 95% CI 0.71-1.25; interaction p-value=0.0298) independent of the type of chemotherapy used Like VEGF-A, PlGF binds and activates signaling through VEGFR2 and it has been a target of active investigation for biomarkers of bevacizumab efficacy. PlGF has been noted as a pharmacodynamic marker with circulating levels consistently increasing in response to bevacizumab, but this is the first report of a potential predictive association between baseline PlGF levels and outcome in CRC. The size and design of CALGB 80405 as a comparison between bevacizumab and cetuximab, rather

TABLE 4

Predictive markers for OS and PFS.

| Marker | Outcome | HR | 95% CI | HR | 95% CI | Interaction p-value |
|---|---|---|---|---|---|---|
| | | FOLFOX/Bev | | FOLFOX/Cetux | | |
| VEGF-D | OS | 1.65 | 1.17-2.33 | 1.12 | 0.81-1.54 | 0.1151 |
| | PFS | 1.70 | 1.19-2.42 | 0.92 | 0.68-1.24 | 0.0097 |
| | | FOLFIRI/Bev | | FOLFIRI/Cetux | | |
| VEGF-D | OS | 0.84 | 0.49-1.45 | 1.10 | 0.54-2.26 | 0.5643 |
| | PFS | 0.95 | 0.61-1.48 | 1.37 | 0.73-2.56 | 0.4336 |
| | | All chemotherapy/Bev | | All chemotherapy/Cetux | | |
| PlGF | PFS | 1.50 | 1.10-2.06 | 0.94 | 0.71-1.25 | 0.0298 |

Note:
HRs and p-values presented are based on continuous marker levels

Discussion

CALGB 80405 is the largest phase III trial to directly compare two commonly used targeted agents, bevacizumab and cetuximab, in metastatic CRC. It provides an important than versus placebo, may have enabled the observation of the unique predictive effect in this study.

Interestingly, while VEGF-D was predictive of PFS benefit from bevacizumab in patients treated with FOLFOX chemotherapy, it did not appear to be predictive in patients receiving FOLFIRI chemotherapy. The predictive effect was largest in patients with VEGF-D levels in the bottom quartile. This closely matched results seen previously in patients with pancreatic cancer treated with gemcitabine and bevacizumab, where low VEGF-D levels were also predictive of benefit from bevacizumab. Importantly, far more patients in this study received FOLFOX (n=523) than FOLFIRI (n=192). It is possible that additional clinical factors related to the use of FOLFOX as opposed to FOLFIRI may confound the VEGF-D effect observed, but the similarity between the VEGF-D predictive effect here with what was previously observed in pancreatic cancer patients indicates it is likely to be generalizable to multiple diseases treated with bevacizumab. In both studies, the predictive effects of VEGF-D were strongest for patients with VEGF-D in the bottom quartile. These findings are similar enough to potentially justify prospective testing of VEGF-D as a pre-specified biomarker of response to bevacizumab. These data suggest that plasma VEGFD levels can be used to identify patients least likely to benefit from bevacizumab, and most likely to benefit from other agents. The predictive impact of VEGF-D and PlGF also suggest that head-to-head comparisons of bevacizumab to ziv-aflibercept may be warranted in biomarker-selected patients.

We claim:

1. A method of treating cancer in a subject, the method comprising:
    obtaining a sample from the subject,
    determining an expression level of VEGF-D and PlGF in a sample from the subject,
    comparing the expression level of VEGF-D and PlGF in the sample to a reference level of VEGF-D of 0.1 ng/mL and PlGF of 5 pg/mL,
    predicting the responsiveness of the cancer to treatment with a cancer therapy, wherein expression levels of VEGF-D and PlGF in the sample higher than the reference level are predictive of lack of responsiveness to a VEGF targeting agent, and
    administering to the subject the cancer therapy when the prediction does not predict a lack of responsiveness, wherein the cancer therapy includes the VEGF targeting agent bevacizumab and an anticancer agent comprising FOLFOX.

2. The method of claim 1, wherein the sample comprises a plasma sample.

3. The method of claim 1, wherein the subject is KRAS wild-type.

4. The method of claim 1, wherein the sample is blood, plasma, serum, or urine.

5. The method of claim 1, wherein the protein expression level is determined by a method selected from ELISA, immunofluorescence, FACS analysis, Western blot, magnetic immunoassays, and antibody-based microarrays.

6. The method of claim 1, wherein the cancer is selected from the group consisting of colorectal, pancreatic, liver, esophageal, gastric, small bowel, cholangiocarcinoma, lung, head and neck, thyroid, melanoma, breast, renal, bladder, ovarian, uterine, prostate, lymphomas, leukemias, neuroendocrine, and glioblastoma or any other form of brain cancer.

7. The method of claim 1, wherein the cancer is colorectal cancer.

* * * * *